(12) United States Patent
Fulmer et al.

(10) Patent No.: US 7,012,255 B2
(45) Date of Patent: Mar. 14, 2006

(54) METHOD OF MEASURING THE CONCENTRATION OF HYDROPEROXIDES OF ALKYLAROMATIC HYDROCARBONS

(75) Inventors: John William Fulmer, Mt. Vernon, IN (US); Andrey Vladimirovich Zinenkov, St. Petersburg (RU); Arkady Samuilovich Dyckman, St. Petersburg (RU); Randall Todd Bishop, Evansville, IN (US)

(73) Assignee: General Electric Company, Schenectady, NY (US)

( * ) Notice: Subject to any disclaimer, the term of this patent is extended or adjusted under 35 U.S.C. 154(b) by 291 days.

(21) Appl. No.: 10/425,909

(22) Filed: Apr. 29, 2003

(65) Prior Publication Data

US 2003/0213911 A1 Nov. 20, 2003

(30) Foreign Application Priority Data

May 20, 2002 (RU) .............................. 2002113195

(51) Int. Cl.
*G01J 5/02* (2006.01)
(52) U.S. Cl. .......................... 250/339.12; 250/339.01; 250/341.2
(58) Field of Classification Search ............ 250/339.01, 250/339.06, 339.07, 339.08, 339.09, 339.12, 250/341.1, 341.2, 341.5
See application file for complete search history.

(56) References Cited

U.S. PATENT DOCUMENTS

| | | | |
|---|---|---|---|
| 2,986,583 A | 5/1961 | Robbers et al. | |
| 3,187,055 A | 6/1965 | Armstrong et al. | |
| 3,305,590 A | 2/1967 | Pollitzer et al. | |
| 3,539,645 A | 11/1970 | Mead et al. | |
| 4,016,213 A * | 4/1977 | Yeh et al. | 568/754 |
| 4,143,080 A | 3/1979 | Harders et al. | |
| 5,254,751 A | 10/1993 | Zakoshansky | |
| 5,530,166 A | 6/1996 | Zakoshansky et al. | |
| 5,684,580 A * | 11/1997 | Cooper et al. | 356/301 |
| 5,717,209 A * | 2/1998 | Bigman et al. | 250/339.12 |
| 5,763,883 A * | 6/1998 | Descales et al. | 250/339.09 |
| 6,057,483 A | 5/2000 | Zakoshansky et al. | |
| 6,070,128 A * | 5/2000 | Descales et al. | 702/30 |
| 6,077,977 A | 6/2000 | Gopinathan et al. | |
| 6,225,513 B1 | 5/2001 | Zakoshansky et al. | |
| 2003/0028355 A1 | 2/2003 | Minati et al. | 702/188 |

FOREIGN PATENT DOCUMENTS

| | | |
|---|---|---|
| GB | 820664 | 3/1957 |
| JP | 2000-63352 | 2/2000 |
| WO | WO 94 27135 A | 11/1994 |
| WO | WO 00 62078 A | 10/2000 |

OTHER PUBLICATIONS

Patent Abstract, Japanese Patent Application Publication No. 2000-63352, published Feb. 29, 2000, 18 pages.
Dong, J. et al., "Stoichiometric Determination of Hydroperoxides in Oils by Fourier Transform Near-Infrared Spectroscopy", Journal of AOAC International, AOAC International, Arlington, VA, vol. 80, No. 2, 1997, pp. 345-352.
Frew, J. E. et al., "Spectrophotometric Determination of Hydrogen Peroxide and Organic Hydroperoxides at Low Concentrations In Aqueous Solution", TROX Report, Gorinchem, NL, vol. 155, 1983, pp. 139-150.
Petruj J. et al., "Trace Determination of Hydroperoxides by Spectrophotometry in Organic Media", Analyst, London, GB, vol. 111, 1986, pp. 671-676.
International Search Report, International Patent Application No. PCT/US03/14616, mailed Oct. 9, 2003.

* cited by examiner

*Primary Examiner*—David Porta
*Assistant Examiner*—Christopher Webb

(57) ABSTRACT

A method for measuring a concentration of a hydroperoxide of an alkylaromatic hydrocarbon in a process stream comprises immersing a probe into the process stream; wherein the probe is coupled to a spectrometer; collecting absorption data with the spectrometer at a wavelength of 13,000 $cm^{-1}$ to 4,000 $cm^{-1}$; and calculating a concentration of the hydroperoxide of the alkylaromatic hydrocarbon in the process stream. In another embodiment, samples are withdrawn from the process stream and analyzed spectrometrically to determine the concentration of the hydroperoxide of the alkylaromatic hydrocarbon in the sample.

14 Claims, No Drawings

METHOD OF MEASURING THE CONCENTRATION OF HYDROPEROXIDES OF ALKYLAROMATIC HYDROCARBONS

BACKGROUND

The present disclosure relates to the area of analytic control, namely to methods of measuring the concentration of hydroperoxides of alkylaromatic hydrocarbons in industrial streams, such as, for example, the measurement of the concentration of cumene hydroperoxide (CHP) in industrial streams obtained during the production of phenol and acetone by a cumene oxidation method.

The industrial two-stage method of producing phenol and acetone involves continuously oxidizing cumene (isopropylbenzene) with atmospheric oxygen to form an intermediate, cumene hydroperoxide (CHP), in a system of sequential reaction vessels as generally shown by reaction scheme (I).

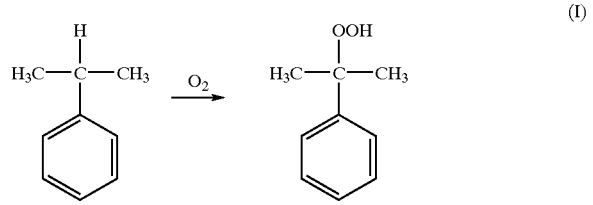

(I)

As shown in reaction scheme (II), the intermediate CHP then undergoes acid decomposition with a protic acid to form the desired end products, i.e., phenol and acetone. The mixture of phenol and acetone that is formed in the process is separated and purified, usually by rectification on several columns.

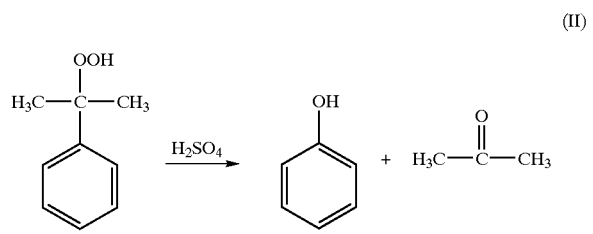

(II)

The economic efficiency of phenol and acetone synthesis by the cumene oxidation method depends, for the most part, on the possibilities of achieving the highest possible yields in the cumene oxidation reaction and at the CHP decomposition stage. Another key factor in the production of phenol and acetone by the cumene method is the safety of production, since both reactions, i.e, the oxidation of cumene and the decomposition of CHP, are exothermic. Moreover, CHP, like many other peroxide compounds, is thermally unstable, requires close monitoring of the reaction conditions, and constant monitoring of the current concentration of CHP in the reaction mixture to ensure the necessary level of production safety.

The yield of CHP obtained during continuous oxidation of cumene in a series of reaction vessels depends on its steady-state concentration, which is maintained in each of the reaction vessels. To obtain a high yield of CHP under safe working conditions, samples of the reaction mixture should be taken as often as possible from all cumene oxidation reaction vessels. The samples are typically hand-carried to the laboratory and analyzed for their CHP concentration by titration methods, which ensures the greatest accuracy and reliability. The same method of manual sampling and titration in the analytic laboratory is used for determining the residual concentration of CHP after the stage of its acid decomposition. Since the stage of continuous decomposition of CHP is especially dangerous, laboratory analyses are done around the clock with a frequency of about 6 to about 12 times per day, which translates to about every 2 to about 4 hours.

Typical laboratory analytical methods of determining the CHP content under industrial production conditions include iodometric titration or a wet photometric method, which involves measuring the optical density after an additional reagent is added to the solution containing CHP. However, both of the indicated methods are rather complex, require the use of expensive reagents, and are not practical for continuous industrial processes, e.g., continuous "in process" or "online continuous" applications.

Another method for monitoring the CHP content includes using an "on-line" industrial calorimeter analyzer. However, the method is generally destructive, indirect, and has only been successfully implemented for use in the CHP decomposition stream. The method includes adding sulfuric acid to a small stream taken off the main stream to completely decompose the CHP. In this method, heat is liberated and the corresponding temperature rise is recorded. The CHP concentration is then calculated from the magnitude of the temperature rise. This method is not attractive for commercial use, since it requires a complex apparatus, uses a complex scheme of streams, and requires an added reagent, which needs to be precisely metered to obtain reproducible results as well as requires frequent replenishment. In addition, this method is generally applicable only for very low concentrations of CHP. Moreover, this method is inconvenient for measurements in the stream at the cumene oxidation stage, since the analysis process consumes a significant quantity of CHP.

Other methods propose using a continuous indirect calorimetric method to monitor the conversion of CHP in a two-stage CHP decomposition process. In these processes, a small stream is diverted from the main stream of the CHP decomposition reaction mixture, and measurements are made in a special calorimetric vessel. The quantity of heat liberated is proportional to the CHP concentration. Measurement of the CHP concentration in the stream at the cumene oxidation stage is not proposed.

Accordingly there still remains a need in the art for a direct, non-destructive, automatic, and relatively instantaneous in-stream measurement process for CHP concentration in industrial streams of the production of phenol and acetone using the cumene method.

BRIEF SUMMARY

Disclosed herein is a "in process" method for measuring a concentration of a hydroperoxide of an alkylaromatic hydrocarbon in a process stream, comprising immersing a probe into the process stream; wherein the probe is coupled to a spectrometer; collecting absorption data with the spectrometer at a wavelength of 13,000 cm$^{-1}$ to 4,000 cm$^{-1}$; and calculating a concentration of the hydroperoxide of the alkylaromatic hydrocarbon in the process stream.

In another embodiment, a method for measuring a concentration of a hydroperoxide of an alkylaromatic hydrocarbon in a process stream, comprising withdrawing a sample from a process stream; collecting absorption data of the sample with the spectrometer at a wavelength of 13,000 cm$^{-1}$ to 4,000 cm$^{-1}$; and calculating a concentration of the hydroperoxide of the alkylaromatic hydrocarbon in the sample.

Also disclosed herein is a process for monitoring a concentration of cumene hydroperoxide during a process for manufacturing phenol and acetone from cumene, wherein the process for manufacturing the phenol and the acetone comprises oxidizing the cumene in an oxidizing atmosphere to produce a process stream containing cumene hydroperoxide, and decomposing the cumene hydroperoxide with a protic acid to produce the phenol and the acetone, the process comprising immersing a probe into the process stream at one or more stages of the oxidizing atmosphere, wherein the probe is coupled to a spectrometer; collecting absorption data with the spectrometer at a wavelength of 13,000 cm$^{-1}$ to 4,000 cm$^{-1}$; and calculating a concentration of the cumene hydroperoxide in the process stream.

The above described and other features are exemplified by the following detailed description.

DETAILED DESCRIPTION

To reduce the time and labor expended in analysis, and also to increase the safety level and decrease the cost of production, it is proposed that a concentration of hydroperoxides of alkylaromatic hydrocarbons in liquid industrial streams at any stages of processes be determined directly using a spectroscopic method. The spectrometer employed in the spectroscopic method is calibrated according to a series of known concentrations of the hydroperoxide solutions, which correspond to a desired range of concentrations that are to be measured. The calibration model obtained from the known concentrations is stored in the memory of a computer by appropriate software. Analysis of a sample for its hydroperoxide content can then be carried out directly in the stream, preferably in a near infrared spectrum, with the concentration of hydroperoxide in the stream being calculated using the calibration model.

The proposed method is based on direct measurement of the concentration of hydroperoxides in liquid industrial streams. This new analytical method is instrumental, and, unlike the prior art, does not propose the use of additional reagents. The given method is spectroscopic, uses the near infrared spectrum of wavelengths and therefore it is non-destructive and makes it possible to obtain precise values of the concentration of hydroperoxides in industrial streams quickly. As used herein, the term near infrared (NIR) is defined as a range of wavelengths of 770 to 2,500 nm, i.e., 13,000–4,000 cm$^{-1}$.

Suitable spectrometers include scanning spectrometers, with a Fourier transform, with sets of filters, and also Raman spectrometers. Other suitable spectrometers will be apparent to those skilled in the art in view of this disclosure.

According to the disclosure, a spectrometer transmission probe made of an inert material is placed in process stream or in a sample. The probe can be employed in a laboratory setting, or more preferably, is disposed in an appropriate pipe on an industrial system for direct measurement of a process stream. The probe can be connected to the spectrometer using fiber-optic cables or the like. When the spectrometer probe is put in the sample, the CHP concentration is measured by reading the spectrum and using the corresponding calibration of the device. Special software for the NIR spectrometer calculates the CHP concentration from the signal that is measured. The analytical procedure is completely finished in 2 to 5 minutes or less, depending on the device that is used, and does not require the use of additional reagents. The NIR spectrometer, the fiber-optic probes, and the equipment connected with them were developed in such a way that they do not contain moving parts (or a minimum number of them), which makes service relatively inexpensive and makes the system highly reliable when installed under production conditions.

A critical requirement for measuring the CHP concentration is first to correctly calibrate the device using standard solutions containing known concentrations of CHP. Nevertheless, this procedure is easy to perform, and the calibration model that is obtained is stable over a long period of time. The standard software for the NIR spectrometer can perform the required calculations on one wavelength at which the absorption is quantitatively connected with the CHP concentration in accordance with the Bouguer-Lambert-Beer law. Measurements at one wavelength are possible; however, it is preferable to use more complex models that are built on several wavelengths, since they ensure better accuracy and reproducibility. These models use several wavelengths, usually no fewer than two wavelengths, which are selected from the NIR spectrum. A calculation algorithm can use multiple linear regression (MLR) or the method of partial least squares (PLS). An important factor in selecting the algorithm is its ability to exclude from the calculation absorption bands from other components that are present in the mixture, such as cumene, phenol, acetone, or the like; these absorption bands are superimposed on those of CHP.

Automatic "on-line" continuous determination of CHP in the commerical process stream at the stages of cumene oxidation and CHP decomposition makes it possible to conduct the process in a safer way compared to the prior art discussed above and has a significant economic effect by giving greater operative control over the process, especially if the data are used immediately in a distributed processing control system. In this case, the controlling machine can use the digital data from the analyzer to optimize the process, with additional data being used to achieve maximum yield and the greatest safety.

In addition to oxidizing cumene, air can also oxidize other hydrocarbons, for example sec-butylbenzene, diisopropylbenzene, and others, to form the corresponding hydroperoxides as intermediates in the production of methyl ethyl ketone, resorcinol, or hydroquinone, and other products.

The method according to the disclosure is rather flexible and can be used both at the cumene oxidation stage and at the CHP decomposition stage. The composition of samples and the component matrix differ significantly in these two cases. For example, the products of cumene oxidation include, in addition to CHP and cumene, which are present in large concentrations, components such as acetophenone, 2-phenyl-2-propanol (dimethylphenylcarbinol, DMPC), and water, while the concentration of CHP in the CHP decomposition reaction mixture is much lower and the basic components of this mixture are cumene, acetone, and phenol. Nevertheless, the CHP concentration can be analyzed quickly and precisely.

The advantages include rapid and precise non-destructive laboratory analysis of the content of cumene hydroperoxide (CHP), which saves time, labor, and reagent expenses; rapid and precise measurement of the CHP concentration at critical areas in the stream: at the cumene oxidation stage and at the stage where CHP is decomposed into phenol and acetone; measurements are made in real time and can be used by the process control system to fine-tune the process in order to obtain the best safety and efficiency indices; and the delay resulting from the necessity of delivering samples to the laboratory and waiting for manual analysis results is eliminated.

The following examples of industrial applicability are presented for illustrative purposes only, and are not intended to limit the scope of the disclosure.

EXAMPLE 1

In this example, a sample of a reaction mixture obtained from the oxidation of cumene by atmospheric oxygen is collected from an industrial system and delivered to the laboratory. Volumetric analysis is performed using iodometric titration as follows: a weighed amount of the sample from the cumene oxidation reaction mixture is placed in a flask having a volume of 200 ml; the weighed amount contained 5 to 10 g if the CHP concentration is 0 to 5%; 1 to 2 g if the CHP concentration is 5 to 25%; and 0.2 to 0.4 g if the CHP concentration is 25 to 85%. 40 ml of a saturated solution of potassium iodide in methanol is added to each sample. Then, a reflux condenser is connected to the flask and the contents are boiled for 5 minutes on a hot plate until the cumene hydroperoxide is completely decomposed. In the process, the hydroperoxide reacts with the potassium iodine and an equivalent quantity of free iodine is liberated. Then, the flask is removed from the hot plate and is allowed to cool for 5 to 10 minutes. After the solution cools, the iodine that was liberated in the preceding step is titrated with a 0.1 N solution of sodium thiosulfate until the color disappears. The number of milliliters of the 0.1 N sodium thiosulfate solution that were used for titration are used to calculate the CHP content according to the following formula.

% $CHP$=(ml of $Na_2S_2O_3$ solution×N×7.61)/sample weight (g)

The results for six comparative samples analyzed in this manner are presented below in Table 1.

For comparison, the same samples were prepared as described above and analyzed for their CHP content in the laboratory using an instrumental spectroscopy method according to the disclosure. The spectrometer used in this example was an Antaris Fourier Transform Near Infrared (NIR) spectrometer produced by Nicolet Instrument Corporation in Madison, Wis. To the spectrometer was connected a fiber-optic transmission probe made of stainless steel, model FPT-850, manufactured by Axiom Analytical Incorporated, Irvine, Calif. The probe was equipped with a head having sapphire windows and an optical path length of 2 cm. The instrument's resolution is reported to be 8 $cm^{-1}$.

In preparation for the analysis of CHP samples, the Antaris FT-NIR spectrometer was first calibrated using a set of standards representing CHP solutions prepared by weight, which spanned the entire range of concentrations that needed to be measured. The calibration curve that was obtained was stored in memory by software. The analysis of six samples of cumene oxidation reaction mixtures using the FT-NIR spectrometer was conducted directly (without sample preparation) and quickly, by placing the fiber-optic probe into the sample that was obtained directly from the factory. No sample preparation or addition of reagents was required. After the probe was placed in the volume containing the sample, the apparatus scanned the spectrum of the sample and measured the absorption at specified wavelengths. In this particular example the ranges are 6,640 to 7,010 $cm^{-1}$ and 8,300 to 8,500 $cm^{-1}$. These two spectral ranges use the partial least squares (PLS) algorithm for analysis. The software automatically calculates the value of the CHP concentration in the sample of the cumene oxidation reaction mixture. The total analysis time for any of the samples was less than 5 minutes. The results of the measurements of six samples are presented in Table 1.

TABLE 1

| Sample Number | CHP Content (by idometric titration) (%) | CHP Content (by NIR method)(%) | Analysis Time (min) | Direct Measurement | Destructive Method |
| --- | --- | --- | --- | --- | --- |
| Comparative 1 | 5.8 | — | 36 | No | Yes |
| Comparative 2 | 10.8 | — | 36 | No | Yes |
| Comparative 3 | 16.3 | — | 36 | No | Yes |
| Comparative 4 | 20.6 | — | 36 | No | Yes |
| Comparative 5 | 28.1 | — | 36 | No | Yes |
| Comparative 6 | 81.7 | — | 36 | No | Yes |
| 1 | — | 5.6 | 5 | Yes | No |
| 2 | — | 10.9 | 5 | Yes | No |
| 3 | — | 16.2 | 5 | Yes | No |
| 4 | — | 20.4 | 5 | Yes | No |
| 5 | — | 28.5 | 5 | Yes | No |
| 6 | — | 81.9 | 5 | Yes | No |

The results presented in Table 1 demonstrate correlation between the analytical methods over the entire range of CHP concentrations using identical samples of cumene oxidation products are used. However, it is noted that the analysis time was significantly reduced when the NIR method was used compared to the iodometric titration method.

EXAMPLE 2

In this example, eight comparative samples were collected at 2 hour intervals from a CHP decomposition reaction vessel of an industrial system for producing phenol and acetone. These samples were delivered to the laboratory and analyzed for the residual concentration of CHP by the prior art method of iodometric titration as described in Example 1. However, a sodium carbonate solution was immediately added to the samples of CHP decomposition reaction mixture as soon as the samples were collected to neutralize the sulfuric acid, thereby stopping the cumene hydroperoxide decomposition reaction. Otherwise, the values of the residual CHP concentration that would be obtained would be too low.

Ten (10) milliliters (ml) of the previously neutralized sample of CHP decomposition reaction mixture were pipetted into a flask, to which 10 ml of acetic acid and 40 ml of a saturated potassium iodide solution in methanol were then added. The contents were refluxed for 5 minutes until the CHP is completely decomposed. In the process, the CHP reacts with the potassium iodine in an equimolar ratio, and free iodine is liberated. Then, the flask is removed from the hot plate and allowed to cool for 5 to 10 minutes. The iodine that was liberated is titrated with a 0.1 N solution of sodium thiosulfate. The CHP concentration was calculated as in Example 1 based on the amount of the sodium thiosulfate solution used for the titration.

The results of the CHP concentration for eight comparative samples are presented below in Table 2.

The same eight samples were also analyzed for their CHP content in the laboratory using an NIR spectrometer. The spectrometer used was an Antaris Fourier transform near infrared (NIR) spectrometer produced by Nicolet Instrument Corporation in Madison, Wis. in accordance with Example 1.

The FT-NIR analysis of the eight samples of cumene decomposition reaction mixtures was conducted directly (without sample preparation) and quickly. The process included transferring 2 mls of neutralized product into a special quartz cell having a size of 8×40 mm. The cell was then placed into the spectrometer, after which the spectrum was read in the given range of wavelengths. For the given analysis a 7-factor model was used that was built according to the method of partial least squares (PLS). The spectral ranges used were 5,770 to 5,720 $cm^{-1}$ and 7,500 to 8,500 $cm^{-1}$. After the spectrum was read, the SPECTROMETER automatically calculated the value of the CHP concentration in each of the eight samples, without operator intervention. Analysis of each sample took less than five minutes and did not require the introduction of additional reagents. The results are presented in Table 2.

factured by Axiom Analytical Incorporated, were inserted into pipes (fluid conduits) in a continuously operating commercial phenol production facility using a multiple stage cumene oxidation system. The transmission probes were put into contact with a liquid reaction mixture exiting from the 1st and 4th oxidation reactors, and detected the presence of CHP. Periodically, the signal from the probes went to a standard NIR spectrometer, which performed a measurement and calculated the CHP concentration. Analyses were carried out using the spectral range of 6,600 to 8,000 $cm^{-1}$. Measurements were carried every 5 to 6 minutes for 5 days, which gave approximately 250 measurements per day. This data, in turn, was transferred in digital form to a computer of a distributed control system produced by the Honeywell Company. The internal analytic data collected during in-process measurement for 5 days is presented in Table 3.

The computer of the distributed control system took the CHP concentration data, which was obtained in-stream, and used it in real time as an input parameter for adjusting various process parameters, for example temperature, to achieve more precise control over the process. As such, it is now possible to increase the yield at the cumene oxidation stage and to conduct the process in a safer and more stable manner. Thus, the introduction of in-stream measurement of the CHP concentration by the spectroscopic method realized a feedback loop in the control of the process. With the introduction of this mode of operation, it was found that there is no need to collect samples of the oxidation reaction mixture and transport them to the laboratory for manual iodometric titration of CHP.

TABLE 2

| Sample Number | CHP Content (by iodometric titration) (%) | CHP Content (by NIR method) (%) | Analysis Time (min) | Direct Measurement | Destructive Method |
|---|---|---|---|---|---|
| Comparative 1 | 1.3 | — | 30 | No | Yes |
| Comparative 2 | 1.1 | — | 30 | No | Yes |
| Comparative 3 | 1.0 | — | 30 | No | Yes |
| Comparative 4 | 0.9 | — | 30 | No | Yes |
| Comparative 5 | 1.0 | — | 30 | No | Yes |
| Comparative 6 | 1.0 | — | 30 | No | Yes |
| Comparative 7 | 1.2 | — | 30 | No | Yes |
| Comparative 8 | 1.3 | — | 30 | No | Yes |
| 1 | — | 1.2 | 5 | Yes | No |
| 2 | — | 1.3 | 5 | Yes | No |
| 3 | — | 1.1 | 5 | Yes | No |
| 4 | — | 0.9 | 5 | Yes | No |
| 5 | — | 1.0 | 5 | Yes | No |
| 6 | — | 0.9 | 5 | Yes | No |
| 7 | — | 1.0 | 5 | Yes | No |
| 8 | — | 1.1 | 5 | Yes | No |

The results demonstrate quantitative correlation between the analyses of CHP by the two methods. The results also show the sensitivity of the NIR spectroscopy method at low CHP concentrations.

EXAMPLE 3

In this "in-process" example, two transmission probes made of stainless steel, which are analogous to those manu-

TABLE 3

| Hours of Operation | CHP Concentration (%) | | Mean CHP Yield (%) | |
|---|---|---|---|---|
| | Reactor 1 | Reactor 4 | Reactor 1 | Reactor 4 |
| 1 | 5–8 | 23–27 | 95.6 | 91.7 |
| 2 | 5–7 | 25–28 | 96.2 | 92.4 |
| 3 | 5–6 | 26–28 | 96.6 | 92.5 |
| 4 | 5–6 | 26–27 | 96.7 | 92.8 |
| 5 | 5–6 | 26–27 | 96.6 | 92.8 |

Table 3 demonstrates that the spectrophotometric method can be successfully used as an online and precise method of analysis of CHP, which makes it possible to reduce fluctuations, increase the stability of process control, and, consequently, to increase the yield of the product and the economic efficiency of the process.

EXAMPLE 4

In this "in-process" example, a transmission probe made of stainless steel, which is analogous to those manufactured by Axiom Analytical Incorporated, was placed in a pipe in a continuously operating CHP decomposition system. The probe had a continuous stream of the CHP decomposition reaction mixture passing through it. In this commercial plant stream, which consisted basically of phenol and acetone, the CHP concentration was measured at a frequency of once every 2 to 3 minutes. The spectrum was scanned, the obtained signal was processed, and the CHP concentration was calculated. The spectral range that was used was 6,000 to 10,000 $cm^{-1}$. Approximately 400 measurements were performed per day, and the tests were carried out over a period of 3 days, i.e., 72 hours.

The analysis data were transferred in digital form to a computer of a distributed process control system, which used the data as an input signal for control. Table 4 presents the data obtained over the 3-day period.

TABLE 4

Analysis of CHP in the CHP decomposition reaction mixture

| Days of Operation | CHP Concentration (%) | Mean α-Methylstyrene Yield (%) |
|---|---|---|
| 1 | 1.2–1.7 | 79.2 |
| 2 | 1.3–1.6 | 82.6 |
| 3 | 1.5–1.6 | 85.5 |

The results shown in Table 4 demonstrate that the spectrometric method successfully be used to measure the concentration of CHP in the stream of a CHP decomposition reaction mixture. This makes it possible to control the course of the process more precisely, obtain a higher yield of the product, and increase the economic efficiency of the process.

EXAMPLE 5

In this example, samples of various hydroperoxides were obtained in a pilot plant and quantitatively analyzed using the spectroscopic method. The data obtained were compared with the data of iodometric titration. The analysis used a spectral range of 5,000 to 10,000 $cm^{-1}$. Analysis of the separate hydroperoxides used parts of this range depending on the nature of the hydroperoxide and other substances present in the mixture. Table 5 presents the results of this analysis.

TABLE 5

| | | Hydroperoxide Content (by iodometric titration) (%) | Hydroperoxide Content (by NIR spectroscopy) (%) |
|---|---|---|---|
| 1 | sec-Butylbenzene hydroperoxide | 8.5–9.0 | 8.8–9.0 |
| 2 | meta-Diisopropylbenzene dihydroperoxide | 7.6–9.2 | 8.0–8.5 |
| 3 | para-Diisopropylbenzene dihydroperoxide | 12.6–13.0 | 12.8–13.1 |

The results presented in Table 5 demonstrate the good quantitative correlation between the standard method of iodometric titration and the spectroscopic method in the NIR spectrum for alkylaromatic hydroperoxides other than CHP.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for measuring a concentration of a hydroperoxide of an alkylaromatic hydrocarbon in a process stream, comprising:
   immersing a probe into the process stream; wherein the probe is coupled to a spectrometer;
   collecting absorption data with the spectrometer at a wavelength of 13,000 $cm^{-1}$ to 4,000 $cm^{-1}$; and
   calculating a concentration of the hydroperoxide of the alkylaromatic hydrocarbon in the process stream, wherein calculating the concentration comprises excluding absorption bands from cumene, phenol, and acetone.

2. The method of claim 1, wherein the alkylaromatic hydrocarbon is cumene and the hydroperoxide is cumene hydroperoxide.

3. The method of claim 1, wherein calculating the concentration of the hydroperoxide comprises determining an absorption calibration curve of known concentrations of the hydroperoxide at a portion of or over the wavelength of 13,000 $cm^{-1}$ to 4,000 $cm^{-1}$.

4. The method of claim 1, wherein the concentration of the hydroperoxide in the process stream correlates to results from an iodometric titration.

5. The method of claim 1, wherein the probe is coupled to the spectrometer with a fiber optic cable.

6. The method of claim 1, further comprising transferring a sample of the process stream to a holder and collecting absorption data of the sample with the spectrometer at a wavelength of 13,000 $cm^{-1}$ to 4,000 $cm^{-1}$.

7. A method for measuring a concentration of a hydroperoxide of an alkylaromatic hydrocarbon in a process stream, comprising:
   withdrawing a sample from a process stream;
   collecting absorption data of the sample with the spectrometer at a wavelength of 13,000 $cm^{-1}$ to 4,000 $cm^{-1}$; and
   calculating a concentration of the hydroperoxide of the alkylaromatic hydrocarbon in the sample, wherein calculating the concentration, comprises excluding absorption bands from cumene, phenol, and acetone.

8. The method of claim 7, wherein calculating the concentration of the hydroperoxide of the alkylaromatic hydrocarbon in the sample comprises determining an absorption calibration curve from known concentrations of the hydroperoxide.

9. The method of claim 7, wherein the concentration of the hydroperoxide in the process stream correlates to results from an iodometric titration.

10. A process for monitoring a concentration of cumene hydroperoxide during a process for manufacturing phenol and acetone from cumene, wherein the process for manufacturing the phenol and the acetone comprises oxidizing the cumene in an oxidizing atmosphere to produce a process stream containing cumene hydroperoxide, and decomposing the cumene hydroperoxide with a protic acid to produce the phenol and the acetone, the process comprising:

immersing a probe into the process stream at one or more stages of the oxidizing atmosphere, wherein the probe is coupled to a spectrometer;

collecting absorption data with the spectrometer at a wavelength of 13,000 $cm^{-1}$ to 4,000 $cm^{-1}$; and calculating a concentration of the cumene hydroperoxide in the process stream, wherein calculating the concentration comprises excluding absorption bands from cumene, phenol, and acetone.

11. The process of claim 10, further comprising withdrawing a sample from the process stream during decomposition of the cumene hydroperoxide; collecting absorption data for the sample with the spectrometer at a wavelength of 13,000 $cm^{-1}$ to 4,000 $cm^{-1}$; and calculating a concentration of the cumene hydroperoxide in the sample.

12. The process of claim 10, further comprising concentrating the cumene hydroperoxide obtained during the oxidation process prior to decomposing the cumene hydroperoxide.

13. The process of claim 10, wherein calculating the concentration of the cumene hydroperoxide in the sample comprises determining an absorption calibration curve from known concentrations of the cumene hydroperoxide.

14. The process of claim 11, wherein calculating the concentration of the cumene hydroperoxide in the process stream or the sample is free of additional reagents or additional sample preparation steps.

* * * * *